United States Patent
Kobayashi

(10) Patent No.: US 7,681,253 B2
(45) Date of Patent: Mar. 23, 2010

(54) COOLING MEMBER FOR USE IN HAT, SUN VISOR OR THE LIKE

(76) Inventor: Toyohiro Kobayashi, 2-11-3, Sumiredai, Yaizushi, Shizuoka (JP) 425-0053

( * ) Notice: Subject to any disclaimer, the term of this patent is extended or adjusted under 35 U.S.C. 154(b) by 188 days.

(21) Appl. No.: 11/918,335

(22) PCT Filed: Mar. 20, 2006

(86) PCT No.: PCT/JP2006/306061
§ 371 (c)(1), (2), (4) Date: Oct. 10, 2007

(87) PCT Pub. No.: WO2006/109545
PCT Pub. Date: Oct. 19, 2006

(65) Prior Publication Data
US 2009/0049578 A1      Feb. 26, 2009

(30) Foreign Application Priority Data
Apr. 11, 2005   (JP)   ............... 2005-140339

(51) Int. Cl.
*A42B 1/24*   (2006.01)
(52) U.S. Cl. .................................................. 2/209.13
(58) Field of Classification Search ............... 2/209.13
See application file for complete search history.

(56) References Cited

U.S. PATENT DOCUMENTS 4,484,363 A * 11/1984 Varanese ............... 2/209.13
4,641,655 A *  2/1987 Abt ........................ 607/109
5,247,928 A *  9/1993 Stilts, Jr. ................ 607/109

FOREIGN PATENT DOCUMENTS

| JP | 62-027617 | 2/1987 |
|---|---|---|
| JP | 9-170108 | 6/1997 |
| JP | 11-61514 | 3/1999 |
| JP | 2000-60892 | 2/2000 |
| JP | 2000-290822 | 10/2000 |
| JP | 2005-42258 | 2/2005 |

* cited by examiner

*Primary Examiner*—Katherine Moran
(74) *Attorney, Agent, or Firm*—Jordan and Hamburg LLP

(57) ABSTRACT

This present invention is for cooling the forehead, face and armpit of a person or imparting cool feeling.

The cooling member comprises a water-absorbing material sheet sandwiched between a flexible planar material provided with a ventilation means, having an adequate hardness, and capable of holding its shape, capable of being bent in a predetermined direction and in the reverse direction a plurality of times, and having a curvature in the predetermined direction and backing cloth having a similar area and a means for dividing the water-absorbing material sheet into parts each having an adequate area corresponding to a vent in such a way that water absorbed in the water absorbing material sheet does not flow out easily into adjacent parts and is used for cooling by allowing the water absorbing material sheet to absorb water and by using its heat of evaporation to cool the surroundings.

The cooling member constitutes a brim portion of a hat, a sun visor or the like, or a pad portion for the forehead, face or armpit of the person and provides a means for imparting a cool feeling to each heat generating portion of the human body.

As preparation for use, the cooling member is dipped into water and bent by applying a force reversely to the curvature in the predetermined direction. Consequently, excess water and water drops are squeezed out easily and uniformly with only the cooling member without wetting the hand of the person.

7 Claims, 6 Drawing Sheets

COOLING MEMBER FOR USE IN HAT, SUN VISOR OR THE LIKE

TECHNICAL FIELD

The present invention relates to a cooling member, wherein a water-absorbing material sheet is incorporated for cooling the forehead, face and armpit of a person or imparting cool feeling by using its heat of evaporation.

BACKGROUND ART

A hat, as disclosed in the following patent document 1, Laid-open Disclosure Public Patent Bulletin No. JP H9-170108, having a cooling member, wherein a water-absorbing fiber or the like is incorporated for cooling the back of the head of a person or imparting cool feeling by using its heat of evaporation, is heretofore known.

Also, techniques relating to cooling the back of the head of a person, as disclosed in the following patent document 2, Laid-open Disclosure Public Patent Bulletin No. 000-60892, as well as patent document 2, Laid-open Disclosure Public Patent Bulletin No. 2000-290822, are heretofore known.

These articles are designed, especially, to directly cover heat generating portions of a wearer's head with a cooling material under the scorching sun.

Patent Document 1: Laid-open Disclosure Public Patent Bulletin No. H8-240941

Patent Document 2: Laid-open Disclosure Public Patent Bulletin No. 2000-60892

Patent Document 3: Laid-open Disclosure Public Patent Bulletin No. 2000-290822

DISCLOSURE OF THE INVENTION

The conventional articles are designed to cool heat generating portions of a human body by direct contact with a cooling material. These articles are not suitable for face and its periphery because they block the view.

Even more, there has not been such an article to secure vision and free motion as well as cooling a wearer's face and its periphery at the same time, while the person is doing sports or outdoor activities.

Women, especially, have a tendency to extremely dislike that the makeup, including foundation, comes off in summer's heat. There is a high demand for such an article that would impart cool feeling on a user's face, without blocking the view by veiling or covering it in doing sports or in fast motion under the scorching sun.

Nor there is such a cooling member provided with a flexible planar material having adequate hardness, capable of holding its shape, having a structure to allow squeezing out excess water easily and quickly without wetting the hands, imparting cool feeling, and applicable as a brim portion of a hat or an underarm pad.

The present invention solves these issues.

The present invention solves these issues by using a cooling member comprising: a planar material made from synthetic resin such as polypropylene, vinyl chloride, polystyrene, or epoxy resin; a backing cloth having good tension and equivalent area as that of planar material; water-absorbing material sheet, sandwiched between the planar material and the backing cloth, water-absorbing material sheet being made of water-absorbing polymer (organic polymer) fiber mainly made from polyvinyl alcohol, polyethylene oxide, or sodium polyacrylate salt, or a sheet made of base materials containing such compounds, or the like, capable of absorbing and retaining water dozens of times of its own weight.

The cooling member having a structure provided with a water-absorbing material sheet therein ordinary water is to be absorbed and excess water can be easily squeezed out without wetting the hand, absorbs heat by heat of evaporation easily without touching a heat generating object such as human body, to impart cool feeling.

In specific, as preparation for use of the present invention, in case it is installed into a brim portion of a hat or a sun visor for example, the brim portion is dipped into water entirely for a certain period of time (about one minute) to impregnate the water-absorbing material sheet. However, excess water should be squeezed out from the cooling member before wearing; otherwise a wearer will be annoyed by dripping water from hem of the brim portion.

However, the planar material, which is human-bendable and adequately hard and flexible, will cause a problem if it is used as the brim portion and is integrated with the water-absorbing material sheet firmly in contact with each other in large area, resulting in too much stiffness that a means to squeeze out excess water, such as twisting or squashing easily like a rag by human hands, is not available.

As a solution to this issue, the present invention uses a structure, wherein the water-absorbing material sheet is sandwiched between the planar material, which is human-bendable and adequately hard and flexible, and the backing cloth, which is elastic to adequate force application. These three elements are glued together or stitched together around hem in adequately wide area.

With this solution, one can hold an article of the present invention in a way that the planar material is placed on the top, the water-absorbing material sheet, impregnating with excess water placed in the middle, and the backing cloth, being elastic with adequate force application placed at the bottom, and then the whole thing is bent in a way that center of the planar material is bent downwards and both ends upwards. This way, large plane of the impregnated water-absorbing material sheet is pressed, thus excess water can be squeezed out uniformly and easily.

If, for example, the planar material is provided with a plurality of holes (hereinafter referred to as 'vent' or 'vents') on it as a ventilation means, these vents provided on the planar material serve as drain holes also, which facilitates squeezing-out action for excess water.

Further, another method is provided wherein the water-absorbing material sheet is divided into small parts according to curvature rate of the planar material, resulting in restriction of inflow of absorbed water between adjacent cells. This is beneficial because excess water, contained in the water-absorbing material sheet, can be squeezed out uniformly, and also heat of evaporation can be provided uniformly while in use.

Also indicated here is a means to maintain the cooling effect for a long time by heat of evaporation: a reservoir is installed near or in integration with the cooling material, the reservoir being connected to the water-absorbing material sheet and supplies water continuously by capillary phenomenon.

DESCRIPTION OF THE SYMBOLS

1. Planar Material
2. Backing Cloth
3. Water-Absorbing Material Sheet
4. Vent
5. Cooling Member
6. Stitches
41. Excess Water and Water Drops
50. Sun Visor
51. Sun Visor Belt
52. Brim Portion
53. Sun Visor Band
61. Air around Face
62. Human Face
71. Human Hand
81. Hat
82. Water-Absorbing Material Extension
91. Underarm Pad
92. Connecting Belt
101. Reservoir
102. Reservoir Water
103. Water-Absorbing Wick
104. Connecting Tube
105. Stitchless Portion
111. Curved Plane near Human Torso Skin
112. Crossed Belt
113. Human Arm
114. Shirt

BEST MODE FOR CARRYING OUT THE INVENTION

Following is a detailed explanation of the present invention in accordance with specific embodiments.

Figure 1:
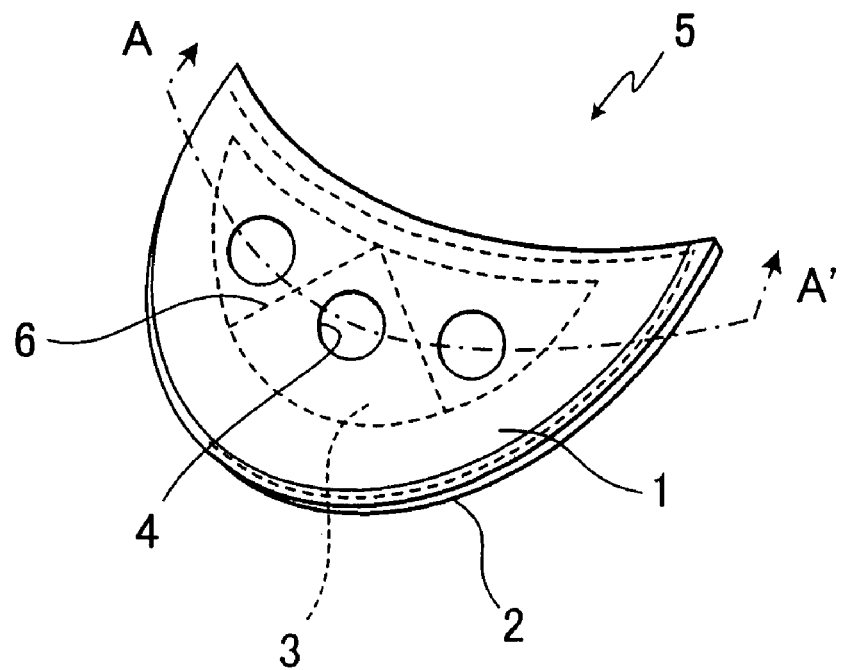
FIG. 1 is a perspective view of components of an embodiment of the present invention.
Figure 2:
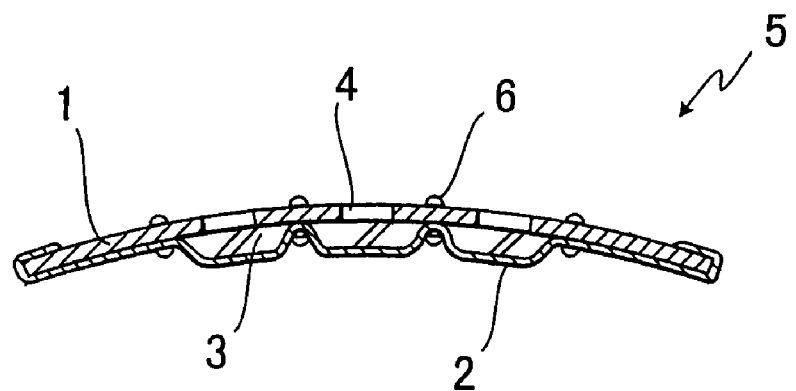
FIG. 2 is a cross-sectional view of a cooling member of the present invention in a state before it is dipped into water

FIG. 1 is a perspective view of constituents of an embodiment. FIG. 2 is a cross-sectional view of cooling member of the present invention, wherein cross-section A-A' shows the cooling member in a state before it is dipped into water.

Cooling member (5) whereof the structure comprises the followings being integrated together by, for examples, stitching or gluing around the hem: the planar material (1) made from flexible synthetic resin, such as polyethylene, polypropylene, polyethylene, or epoxy resin which is adequately hard and capable of holding its shape; the backing cloth (2) having equivalent area to that of the planar material (1) and having good tension; fiber structure, sandwiched between the planar material (1) and the backing cloth (2), a fiber sheet being made of organic high polymer mainly consisting of polyvinyl alcohol, sodium polyacrylate salt, and polyethylene oxide; a water-absorbing material sheet (3), or the like, also sandwiched between the planar material (1) and the backing cloth (2), the water-absorbing material sheet being made of fibers made from paper substrate wherein the compounds are contained, the water-absorbing material sheet being capable of absorbing and retaining water dozens of times the weight of it.

Also, the planar material is provided with a plurality of vents (4), and the water-absorbing material sheet is divided into parts by the split ratio corresponding to curvature of the planar material. Dividing structure is made in such a manner that the planar material and the backing cloth are sewn together with stitches (6), or heat-shielded to each other, or the like, into small parts with a purpose that the water absorbed in the water absorbing material sheet does not flow out easily into adjacent parts.

The split ratio depends on the curvature of the planar material: the smaller (looser) the curvature the less number of divided parts are; the greater (tighter) the curvature the more effectively the tension of the backing cloth is.

The cooling member in FIG. 1 shows an example of three-part-split, based on a typical curvature in case of being installed into a brim portion of a hat or a sun visor.

Referring now to actions of cooling member of the present invention.

Figure 3:
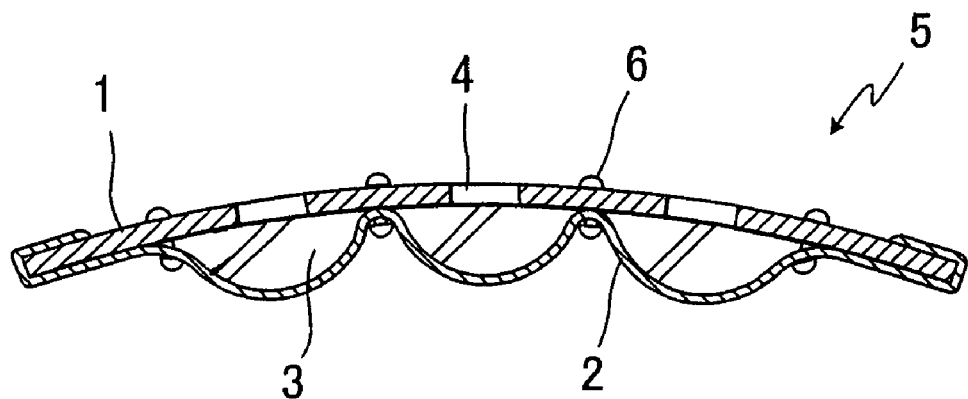
FIG. 3 is a cross-sectional view of the cooling member of the present invention when a certain period of time has passed after it is entirely dipped into water.

FIG. 3 is a cross-sectional view, in section A-A', of the cooling member of the present invention in a state that a certain period of time has passed after it is entirely dipped into water.

In comparison with FIG. 2, FIG. 3 shows the water-absorbing material sheet being extremely impregnated after absorbing water into each divided part.

In this condition, each divided part of the water-absorbing material sheet (3) contains excess water, which drips in the form of water drops from hem of the water-absorbing material sheet (3), the planar material (1), and the backing cloth, so that it is not suitable for the cooling member (5) which shall obtain heat of evaporation effectively. Therefore, the excess water needs to be squeezed out, but the planar material (1) having adequate hardness, and the water-absorbing material sheet (3) are installed as to be in full contact with each other in curvature shape, so that they cannot be twisted for squeezing out water just like the way one would twist a soft towel or rag, containing water, by holding both ends of it.

Figure 4:
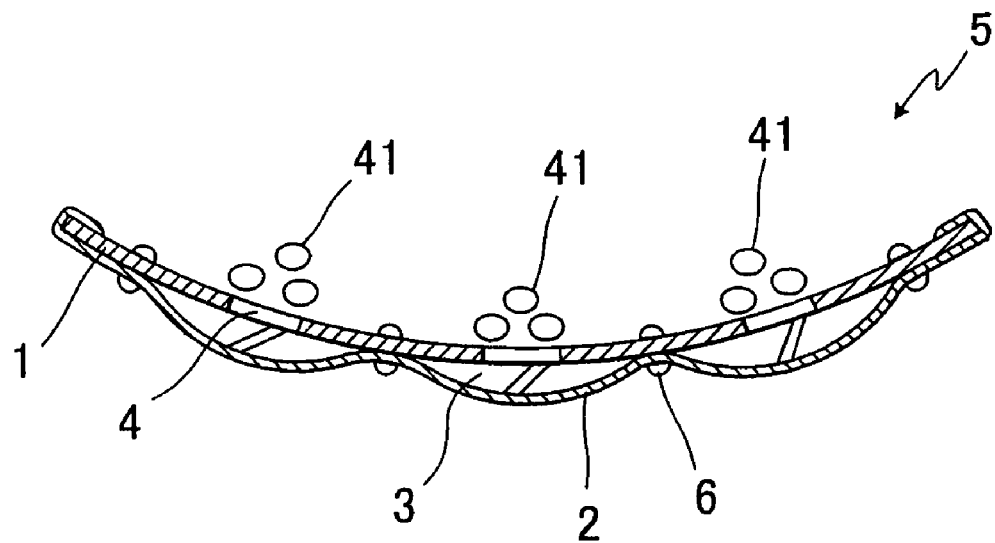
FIG. 4 is a cross-sectional view of a planar material of the present invention when it is reverse-bent.
Figure 7:
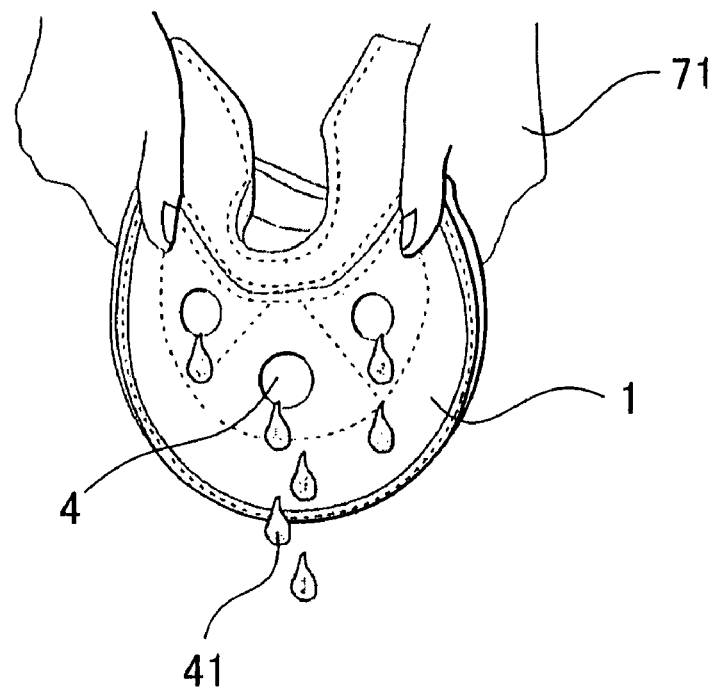
FIG. 7 is a drawing showing a state when excess water is being squeezed out and drained.

The solution is described in FIG. 4 and FIG. 7. FIG. 4 shows a state in which the planar material of the present invention is bent in the reverse direction. FIG. 7 shows a state in which the excess water is squeezed out from the cooling member installed into the present invention from a sun visor, for example.

Now, the planar material (1) is bent by applying a force reversely to the curvature with its center downwards and its ends upwards as shown in FIG. 7. FIG. 4 indicates that tension is generated in each divided part of the backing cloth (2), the water-absorbing material sheet, sandwiched between the backing cloth (2) and the bottom surface of the planar material (1) for the brim portion, are compressed for each divided part, so that the excess water and water drops (41) can be squeezed out from each divided part, can be drained easily through the vent (4) corresponding to each divided part on the planar material (1).

Furthermore, applying the force can be done easily with only the cooling member without wetting the hand (71) of the person.

The backing cloth (2) can be any general fabric having water and moisture permeability. However, if such a means with which moisture permeates but water does not, if a waterproof and moisture permeable fabric is used for example, higher compression force can be applied in the each small divided part, helping to drain excess water (41) fast through the vent (4). Further, when water contained in the water-absorbing material sheet (3) evaporates, moisture permeates through the each divided part, so that the cooling member of this present invention can be cooled uniformly.

Figure 9:
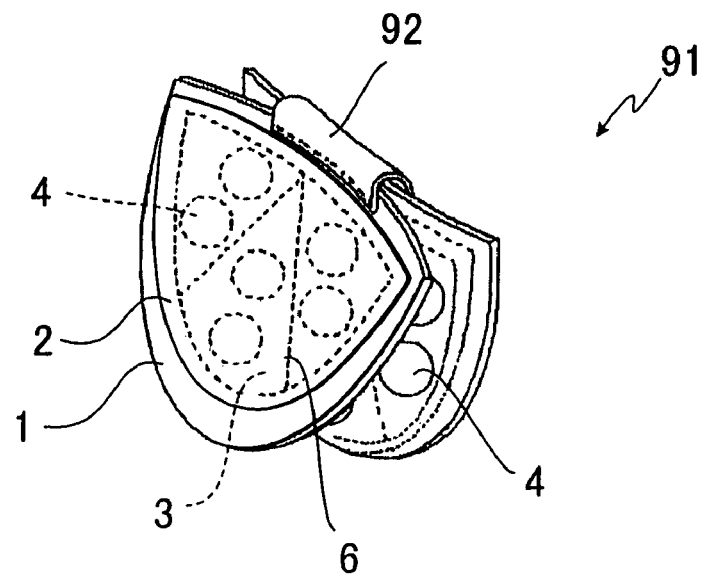
FIG. 9 is a drawing of the cooling member of the present invention used as an underarm cooling pad.
Figure 11:
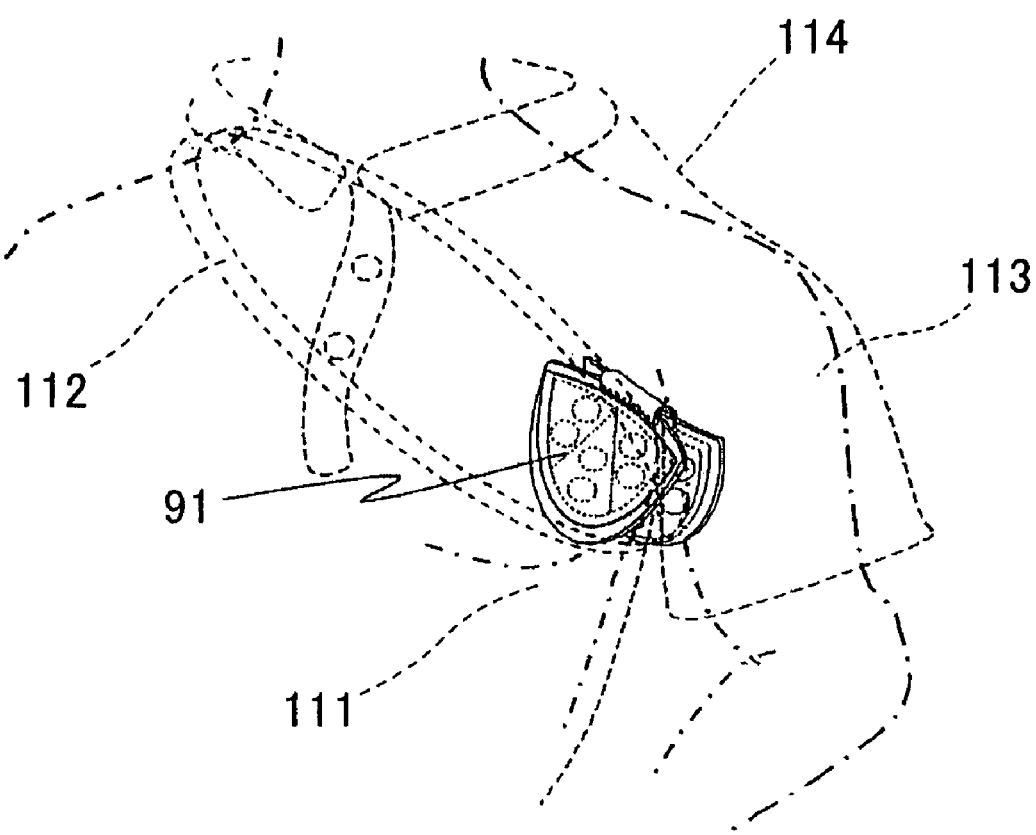
FIG. 11 is a drawing illustrating a state wherein the cooling member of the present invention is cooling an armpit.

The waterproof and breathable fiber used for the backing cloth (2) is dry to the skin and also, in use, it is on the inner side of the curvature of the planar material, thus, in the structures of the brim portion of a hat (81) the fiber is designed to be on the inner curvature, and in an example of that of the underarm pad (91) shown in FIG. 9, it is designed to touch the curved plane near human torso skin (111) as clearly demonstrated in FIG. 11.

In this case, one can place the waterproof and breathable fiber, used as the backing cloth (2) for the underarm pad (91), inside of a shirt (114) right under the wearer's armpit, so that the shirt does not get wet by sweat, and cool feeling can be imparted on the armpit.

In the composition of the present invention, the vent (4) is one example of ventilation means. It is obvious that the same effect can be achieved also with either a mesh material made from the flexible synthetic resin or the like, or the planar material having many small vents. The backing cloth is explained herein with an example of the waterproof and breathable fiber, however, a material having similar feeling to that of human skin and having planar tension is more favorable.

Figure 5:
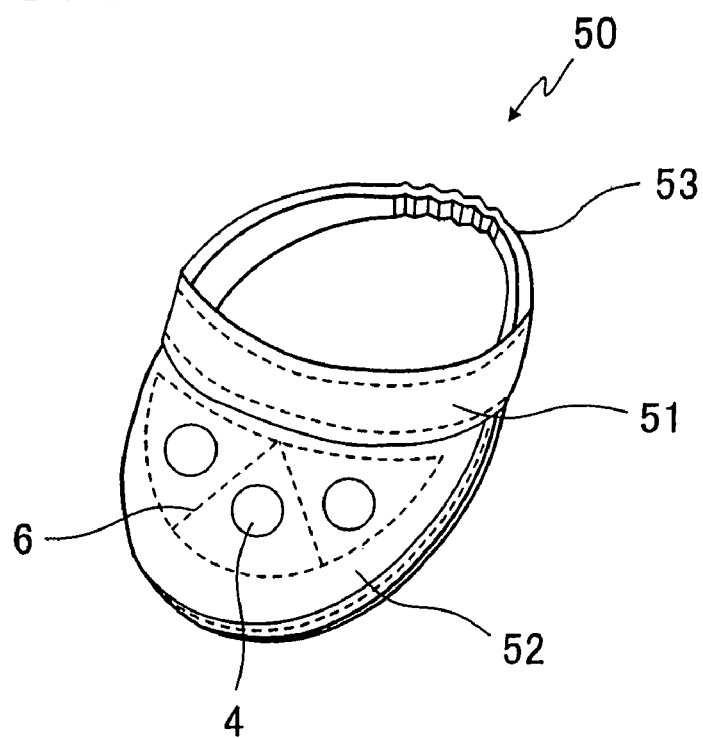
FIG. 5 is a drawing of the cooling member of the present invention installed into a sun visor.

FIG. 5 shows the cooling member of the present invention installed into a sun visor. The sun visor (50) comprising the cooling member (5) connected to and stitched together with a belt (51) which touches the wearer's forehead. 52 is the planar material (1) used as the brim portion of the sun visor.

Figure 6:
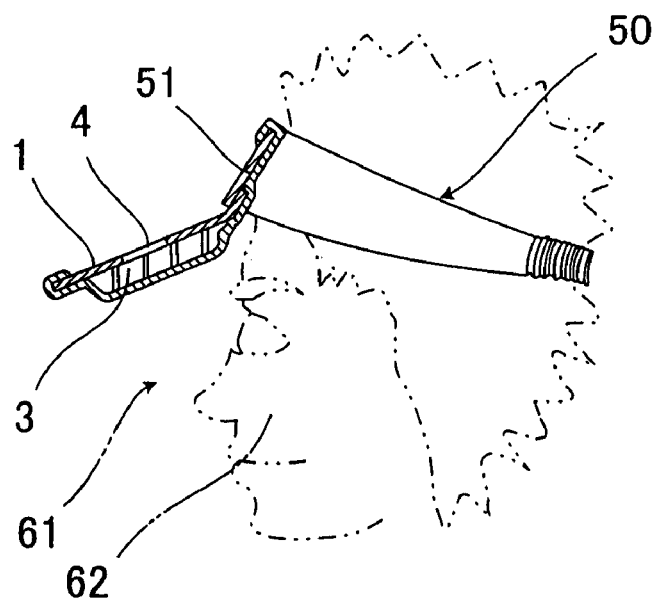
FIG. 6 is a side view of the cooling member of the present invention installed into a sun visor being worn by a person.

Further, FIG. 6 illustrates the cooling member of the present invention installed into the sun visor (50) being worn by a person. 62 is a human face. The water-absorbing material sheet (3) is installed into the planar material (52) (the brim portion) of the sun visor and the water evaporates through the backing cloth (2) and the vent (4), cooling the air around the face (61) which is the face being a heat generator.

Experiments indicate that the cooling member of the present invention cools down the air around the face (61) right beneath the brim portion by 3° C. in the calm ambient temperature of 30° C., in comparison with the condition not using the cooling member.

This is sufficient enough for imparting cool feeling on the face (62) under the scorching sun, reduce sweating from the face (62), and thus effectively protect makeup for women from coming off.

Figure 8:
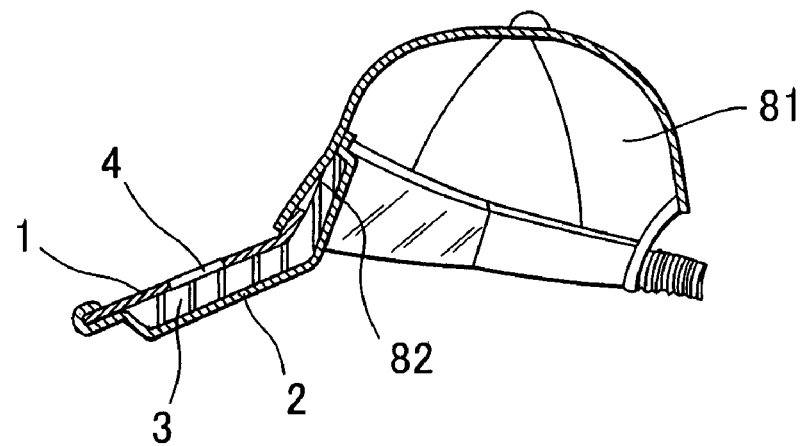
FIG. 8 is an embodiment of the cooling member of the present invention installed in a cap.

FIG. 8 shows an embodiment of the cooling member of the present invention installed into a cap.

In this drawing, 81 is a cap body, and 82 is an extension of the water-absorbing material sheet (3), being connected with a belt so that it makes contact with forehead of a person when the cap is worn.

This way, when used in a sun visor or a hat, the water-absorbing material sheet (3) cools the face (62) by non-contact, and the sun visor belt (51) cools the forehead by direct contact, imparting cool feeling in a synergistic manner. Further, the water-absorbing material extension (82) will make the entire capacity of the water-absorbing material relatively large, rather than the case being incorporated into the brim portion of a cap, serving also as a water supply layer, and as a result, longer time of heat of evaporation can be expected.

On the other hand, providing a separation or partition means between the water-absorbing material sheet (3) and the water-absorbing material extension (82), enables two-way usage of this article, which is advantageous for those who do not want their foreheads get wet, especially for women when they are wearing makeup. A user can choose either dipping only the water-absorbing material sheet (3) into and retain water, while keeping the water-absorbing extension (82) dry to be used for absorbing sweat, or dip both of them into water if one would not mind getting the forehead wet for the sake of imparting cool feeling.

Further, this invention can be composed for use at other portions of a body. For example, in case it is applied as a shading cover to cool the back of the head or the nape where blood flow is large, the shading cover, similar to the brim portion having a curvature, imparts cool feeling on the back of the head and the nape, without the water-absorbing material sheet and the backing cloth touching the nape skin.

The curvature-shape structure like the brim portion is also applicable to armpit, inner thighs or the like where blood flow is large. FIG. 9 shows an application as an underarm cooling pad (91), therein the cooling member shown in FIG. 1 is used in a pair provided with a connecting belt (92) between each pad.

In this case, the planar material (1) shall be made of urethane foam resin, fluorine resin or the like, having adequate hardness and gentle touch to human skin.

As described above; by dipping the pad (91) into water, and then bent the curvature in the reverse direction, squeezing out excess water, and as shown in FIG. 11, placing on the joint seam between torso portion and sleeve portion of a shirt, blouse, work cloth or the like, or firmly fixing with a crossed belt (112), it can cool both torso side as well as arm (113) side of a person's armpit at the same time.

In this case, if excess water is drained from the underarm pad (91) comprising the cooling member of this present invention, a user would suffer extreme discomfort because armpit is a very sensitive area. The present invention, as described above, enables that excess water in the water-absorbing material sheet (3), even though it is installed into the planar material (1), can be squeezed out easily and completely before use, thus a user can feel pleasantly cool on the armpit. Also, providing with a cross-belt (112), for example, firmly keeps the pad underarm in fast motion, while preventing the shirt (114) from getting wet.

If the present invention does not comprise the planar material but a plain cloth, the cooling member placed underarm of a person would not stay put but lose its shape and gets bulky even by a slight motion, making the user uncomfortable to use it for a long time. The present invention solves this problem.

Figure 10:
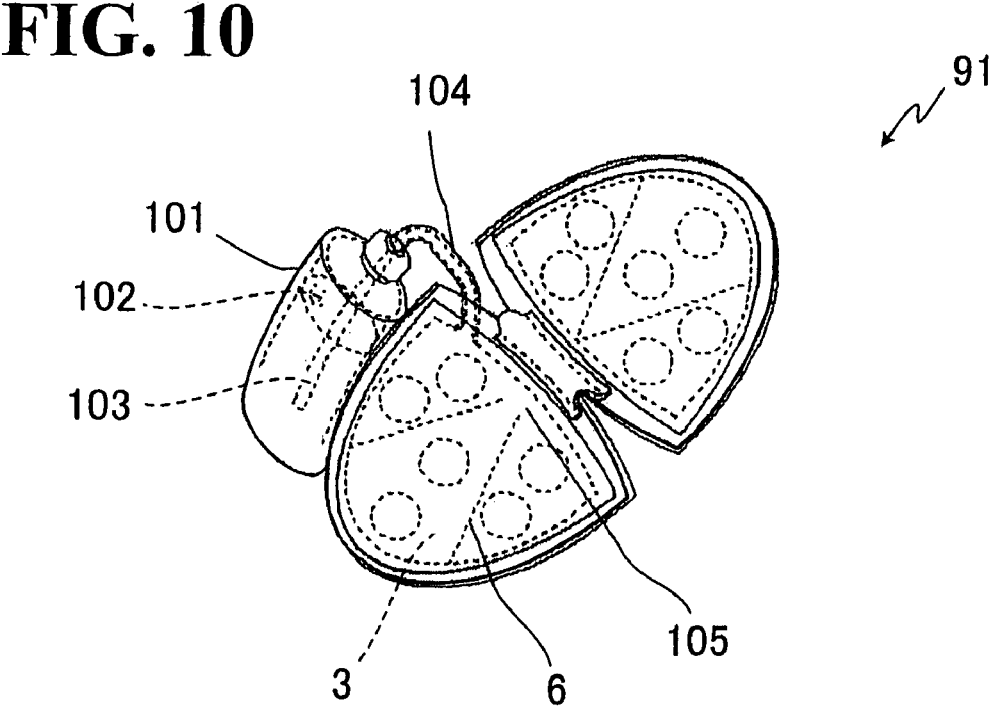
FIG. 10 is a drawing of the cooling member of the present invention equipped with a reservoir.

Also, FIG. 10 shows the underarm pad (91) comprising the cooling material for cooling an armpit, provided with a reservoir (101), therein a water-absorbing wick (103) comprising a torsade, made from the same material as used for the water-absorbing material sheet (3), in order to obtain a means to provide water continuously to the water-absorbing material sheet (3) by using capillary phenomenon, the water-absorbing wick being connected to the water-absorbing material sheet (3) through a connecting tube (104).

In this case, stitchless portion (105) is provided, where stitch (6) is partially omitted from the parting line in such a manner that the water-squeezing action is not affected, while the water from the reservoir spreads out completely in the divided water-absorbing material sheet.

This enables to keep the water-absorbing material sheet (3) cooled until the entire water in the reservoir (101) runs out.

INDUSTRIAL APPLICABILITY

This present invention is effective in the followings:

1. The present invention has a structure comprising the plastic planar material, the backing cloth, and the water-absorbing material sheet sandwiched between them, and can be bent by applying a force reversely to the curvature in the predetermined direction (as in the shape in use) resulting in that excess water and water drops are squeezed out easily from the water-absorbing material sheet without wetting the hand of the person, and helps acceleration of even evaporation of water.

2. The present invention further provides a structure comprising the plastic planar material, the backing cloth, and the water-absorbing material sheet sandwiched between them, and a means for dividing those into parts each having an adequate area corresponding to a vent, by which action of evaporation heat is enhanced and accelerated.

Furthermore, the cooling member can be bent by applying a force reversely to the curvature as is when used. Consequently, excess water and water drops are squeezed out easily without wetting the hand of the person.

3. The water-squeezable structure can be provided by changing division number corresponding to curvature rate of the planar plastic material, resulting in such a great effect that water content in water-absorbing material sheet can be adjusted to appropriate level for evaporation to start.

4. Furthermore, cooling member of the present invention is provided as a brim portion of a hat or a sun visor, therein, as described before, adequate water content in water-absorbing material sheet absorbs heat in the space between it and heat generating portion of head of a person when the water evaporates, thus imparting cool feeling on the face while the user is doing exercise, sports or activities in outdoors in summer's heat. This feature is especially beneficial for women to keep their makeup stay put and protect it from coming off from the face.

This is extremely helpful and effective for those people, for example, who want to have cool feeling on their faces to soothe hot flash when they are in tennis/golf games, but do not want to get their hands wet to keep good grip on their tennis rackets or golf clubs.

5. Furthermore, by employing waterproof breathable fabric for the backing cloth, higher pressure is generated in water-absorbing fabric containing excess water, which will be squeezed out faster and easier, with less curvature rate of the brim of a cap, less force, and shallower bending angle These features, i.e. the brim portion of a cap can be back to the original shape easily with less curvature rate, are greatly beneficial in term of design to hold its shape while in use.

6. Also, such an application that the water-absorbing material sheets are jointed to be used for a brim portion of a cap or a sun visor as well as a belt, therewith a human forehead contacts directly.

7. Furthermore, this present invention is applicable, not limited to as a brim portion of a sun visor or a hat, but as a shading cover for back part of the head or the nape of a person, or as a cooling device to cool portions of a human body having a curvature, such as an armpit, all of where blood flow is large, for protection from heat stroke.

8. Furthermore, as designated in FIG. 10, a reservoir can be equipped near or in integration with the cooling member of the present invention, provided with a means of guiding the reservoir water to the water-absorbing material sheet by capillary phenomenon, enabling long-time continuous evaporation from the water-absorbing material sheet until the reservoir runs out of water.

The invention claimed is:

1. A cooling member for a hat or the like comprising a flexible planar material having an adequate hardness, and capable of holding its shape, capable of being bent in a predetermined direction and in the reverse direction a plurality of times, and having a curvature in the predetermined direction, a backing cloth having an area similar to that of the planar material, and a water-absorbing material sheet to absorb water and cool the surroundings by using its heat of evaporation, and comprising a plurality of arcuate portions which correspond to the curvature of the planar material therethroughout.

2. A cooling member as claimed in claim 1, wherein the cooling member comprises
   the planar material, the backing cloth and the water-absorbing material sheet being sandwiched between them, having adequate areas corresponding to the curvature in the predetermined direction, and provided with a means that water absorbed in the water absorbing material sheet does not flow out easily into adjacent parts.

3. A cooling member as claimed in claim 1 or 2, wherein the planar material is provided with a ventilation means.

4. A cooling member as claimed in claim 1 or 2, wherein the backing cloth is made of water-resistant breathable fabric.

5. A cooling member as claimed in claim 1 or 2, wherein the cooling member is incorporated into a sun visor or a brim portion of a cap.

6. A cooling member as claimed in claim 1 or 2, wherein the cooling member imparts a cool feeling near an armpit of a person.

7. A cooling member as claimed in claim 6, wherein the cooling member comprises a water reservoir provided with a means to guide the reservoir water to the water-absorbing material sheet, the water-absorbing material sheet cools an armpit of the person.

\* \* \* \* \*